(12) United States Patent
Forgacs et al.

(10) Patent No.: US 10,669,524 B2
(45) Date of Patent: Jun. 2, 2020

(54) LARGE SCALE CELL CULTURE SYSTEM FOR MAKING MEAT AND ASSOCIATED PRODUCTS

(71) Applicant: FORK & GOODE, INC, Nutley, NJ (US)

(72) Inventors: Gabor Forgacs, New York, NY (US); Niyati Gupta, New York, NY (US)

(73) Assignee: FORK & GOODE, INC., Nutley, NJ (US)

( * ) Notice: Subject to any disclaimer, the term of this patent is extended or adjusted under 35 U.S.C. 154(b) by 0 days.

(21) Appl. No.: 16/112,171

(22) Filed: Aug. 24, 2018

(65) Prior Publication Data

US 2019/0376026 A1    Dec. 12, 2019

Related U.S. Application Data

(60) Provisional application No. 62/684,087, filed on Jun. 12, 2018.

(51) Int. Cl.
| | |
|---|---|
| C12N 5/00 | (2006.01) |
| C12N 5/071 | (2010.01) |
| C12M 1/32 | (2006.01) |
| A23L 13/40 | (2016.01) |
| A23L 33/10 | (2016.01) |
| C12M 1/00 | (2006.01) |

(52) U.S. Cl.
CPC ............ *C12N 5/0037* (2013.01); *A23L 13/45* (2016.08); *A23L 33/10* (2016.08); *C12M 23/12* (2013.01); *C12M 29/00* (2013.01); *C12N 5/0062* (2013.01); *C12N 5/0697* (2013.01); *A23V 2002/00* (2013.01); *C12N 2500/90* (2013.01); *C12N 2513/00* (2013.01)

(58) Field of Classification Search
None
See application file for complete search history.

(56) References Cited

U.S. PATENT DOCUMENTS

| | | | | |
|---|---|---|---|---|
| 2015/0079238 A1* | 3/2015 | Marga | ................ | C12N 5/0658 426/92 |
| 2015/0225685 A1* | 8/2015 | Hirschel | ................ | C12M 23/42 435/70.1 |

OTHER PUBLICATIONS

Bhat et al. "Tissue engineered meat—Future meat" Journal of Stored Products and Postharvest Research vol. 2(1), pp. 1-10, Jan. 2011 (Year: 2011).*
Sen et al. "Passaging Protocols for Mammalian Neural Stem Cells in Suspension Bioreactors" Biotechnol. Prog. 2002, 18, 337-345 (Year: 2002).*
Singh et al. "Up-scaling single cell-inoculated suspension culture of human embryonic stem cells" Stem Cell Research (2010) 4, 165-179 (Year: 2010).*
Allan et al. "Bioprocess Design Considerations for Cultured Meat Production with a Focus on the Expansion Bioreactor" frontiers in Sustainable food systems Jun. 2019, vol. 3, Article 44, 9 pages (Year: 2019).*
Edelman PD, McFarland DC, Mironov VA, Matheny JG. "In vitro-cultured meat production." Tissue Eng. May-Jun. 2005; 11(5-6):659-62. (Year: 2005).*
Kumar et al. "Large scale industrialized cell expansion: producing the critical raw material for biofabrication processes" Biofabrication 7 (2015) 15 pgs (Year: 2015).*
Merten et al. "Advances in cell culture: anchorage dependence." Phil. Trans. R. Soc. B 2015, 370: 20140040, 22 pages (Year: 2015).*

* cited by examiner

*Primary Examiner* — Thane Underdahl
(74) *Attorney, Agent, or Firm* — Wilson Sonsini Goodrich & Rosati

(57) ABSTRACT

Provided is a large-scale cell culture system for producing products without harming animals. Also provided is a method for making meat products using this cell culture system. Further provided is a method for making personal care products using this cell culture system, as well as a method for making nutritional supplements using this cell culture system.

10 Claims, 4 Drawing Sheets

LARGE SCALE CELL CULTURE SYSTEM FOR MAKING MEAT AND ASSOCIATED PRODUCTS

FIELD OF INVENTION

Described herein is a large scale cell culture system, as well as methods of making and using it to form engineered meat products, nutritional supplements and personal care compositions. An important element of the invention is that the culture system does not require the use of serum (e.g. fetal bovine serum) an animal derived substance.

BACKGROUND

The human body needs nutrients to be delivered to each of its cells. Once food is decomposed into digestible and non-digestible components, the digestible components are subsequently processed into micronutrients and eventually delivered to the various organs, tissues and cells mainly via the circulatory system. The complex molecules, such as growth factors, cytokines, etc. that are also needed for the healthy functioning of the organism are produced by the organism itself from the basic nutrients processed from the food intake. This way the organism represents a highly autonomous system.

This system is mimicked in the organ-on-the-chip device, a microphysiological system, where organoids prepared from specialized cells and modeling the various organs of the body are coupled through microfluidic channels representing the circulatory system that carries the nutrient-containing culture medium supplied from the exterior. These organ-on-the-chip devices are used as toxicology assays in drug development to supplement animal models and hoped one day to replace animal trials. The organoids used in these devices (prepared separately and then inserted into the device) are miniature representations of tissues and organs with linear dimensions typically on the order of a few hundred microns.

The cell culture medium circulated (i.e. pumped) in the microphysiological circuit contains a multitude of molecules necessary for the healthy maintenance and growths of cells. An important component of such medium is typically serum such as fetal bovine serum (FBS), calf serum, or horse serum. The sera, in particular PBS, require the slaughtering of animals. FBS is also expensive and shows wide variation front animal to animal.

The nutritional benefits of meat are tempered by potential associated environmental degradation. According to a 2006 report by the Livestock, Environment And Development Initiative, entitled Livestock's Long Shadow—Environmental Issues and Options, the livestock industry is one of the largest contributors to environmental degradation worldwide. Modern practices of raising animals for food contributes widely to air and water pollution, land degradation, climate change, and loss of biodiversity. The production and consumption of meat and other animal sources of protein is also associated with the clearing of rainforests and species extinction. This has led to a significant effort to develop clean meat. As used herein, clean meat means providing meat without harming animals. Most efforts are based on growing and culturing mammalian cells that require growth medium with components derived from slaughtered animals for example, fetal bovine serum. Accordingly, there is a need for an alternative growth method for meat produced without harming animals.

Proteins are also used in personal care applications and nutritional supplements. For example, proteins are applied to the face to improve the appearance of skin. Protein bars and protein powders are ingested as nutritional supplements. There is a continuing need for protein solutions for personal care and alternatives for nutritional supplements.

The inventors have previously described engineered meats and methods of making engineered meats using cultured cells. See, e.g., U.S. Pat. No. 8,703,216, titled "ENGINEERED COMESTIBLE MEAT," hereby incorporated by reference in its entirety. However, bio-manufacturing processes aimed at building extended tissue constructs that require large numbers of adherent cells face the difficulty of growing these cells (to the billions to trillions) efficiently and cost effectively. Additionally, the medium required to grow the cells typically include fetal bovine serum which is frowned upon for the reasons cited above and may also be expensive.

SUMMARY OF THE INVENTION

An objective of the present invention is to provide a large-scale cell culture system for producing products without harming animals. Another objective of the present invention is to provide a method for making meat products using this cell culture system. Yet another objective of the present invention is to provide a method for making personal care products using this cell culture system. Finally, an objective of the present invention is to provide a method for making nutritional supplements using this cell culture system.

The above objectives highlight certain aspects of the invention. Additional aspects and embodiments of the invention are found in the following detailed description of the invention.

FIGURES

A more complete appreciation of the invention and many of the attendant advantages thereof will be readily obtained as the same become better understood by reference to the following Figures in conjunction with the detailed description below.

DETAILED DESCRIPTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The cell culture system of the present invention includes one or more vessels.

Figure 1:
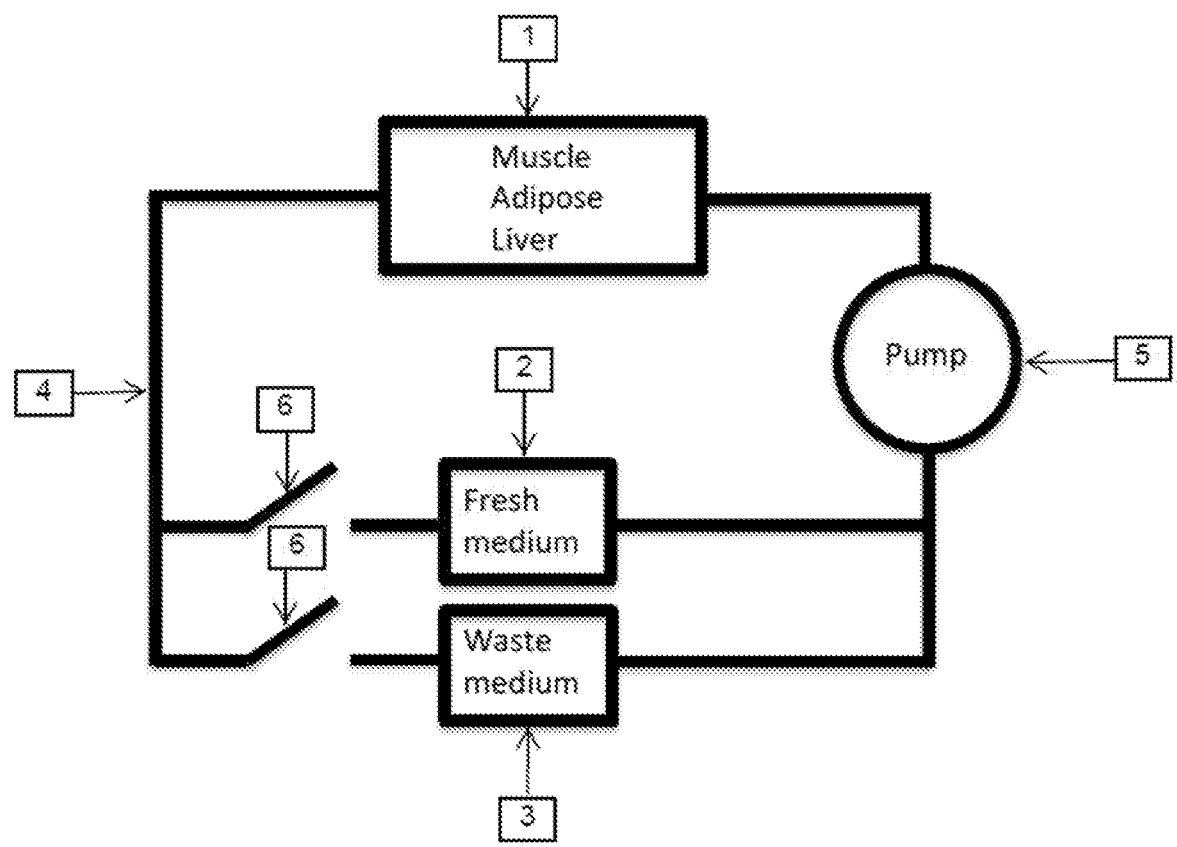
FIG. 1 shows an example of a large-scale cell culture system according to the present invention, wherein different cell types are cultured in a single culturing vessel.

In an embodiment of the invention, a single culturing vessel may be used to culture the various cell types together. As shown in FIG. 1, culturing vessel 1 contains adipose, muscle and liver cells. Vessel 1 is connected to fresh medium vessel 2 and waste vessel 3 by line 4. Medium is pumped through the lines into the vessels with pump 5. Valves 6 controls the flow to the vessels, when the valve to the fresh medium vessel is open, the valve to the waste vessel is closed and visa versa. This approach may make the cells function better than when cultured independently, far example, by secreting their relevant growth factors more efficiently.

It is envisioned within the present invention that when two or more culturing vessels are used they are connected in parallel or in series or a combination of the two.

The vessels may also be referred to as bioreactors. The system allows culturing of one or several cell types (each in its own culturing vessel) at the same time. Alternatively, several cell types may be cultured in a single culturing vessel either as part of a mixture or independently cultured in isolation separated by partitions or separators. The cell types may be of different genus and/or species or may be of the same genus and species, but belong to different sub-types. Alternatively, the cell types may be of the same genus and species, but differ from each other based on the biopsy they are obtained from.

Figure 2:
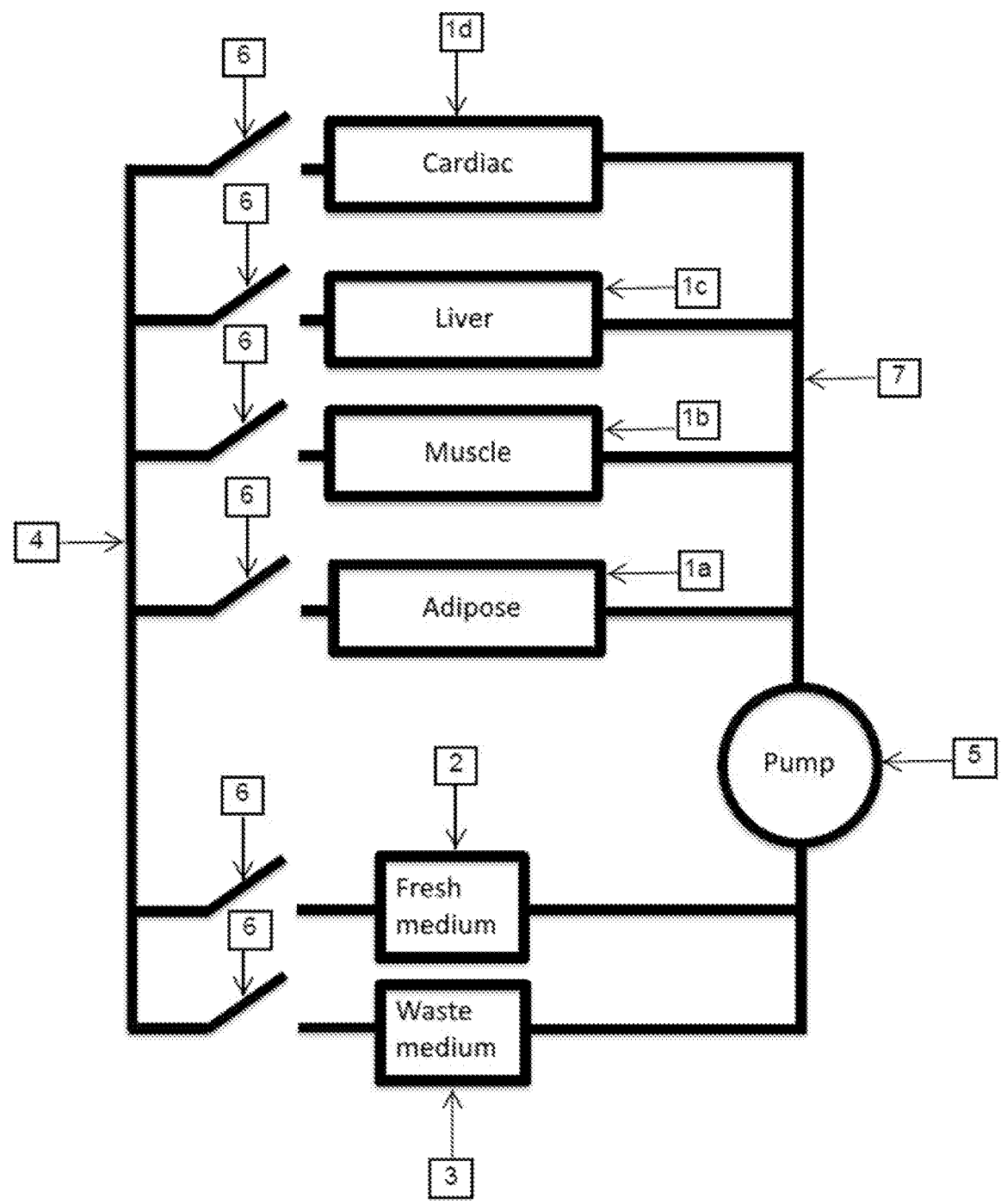
FIG. 2 shows an example of a large-scale cell culture system according to the present invention, wherein different cell types are cultured in separate culturing vessels and the culturing vessels are connected in parallel.

As used herein, "vessels connected in parallel" means two or more culturing vessels are fed from a manifold at the same time, in other words, a fluid flows from a pump through a manifold which distributes the fluid to the culturing vessels evenly and simultaneously and loops back to the pump. The fluid for use in the invention is referred to as culture medium. The term is also envisioned to mean that, in a mixed parallel and in series arrangement, at least one culturing vessel is connected in parallel relative to the in series circuit containing two or more culturing vessels connected in series. As shown in FIG. 2, culturing vessel 1a contains adipose cells, vessel 1b contains muscle cells, vessel 1c contains liver cells and vessel 1d contains cardiac cells. The culturing vessels are connected to fresh medium vessel 2 and waste vessel 3 by line 4. Medium is pumped through the line 4 into the vessels with pump 5. The medium flows from the pump to the manifold 7 through line 4, then in parallel through vessel 1a, 1b, 1c and 1d. Valves 6 control the flow to the vessels, when the valve to the fresh medium vessel is open, the valve to the waste vessel is closed and visa vice versa.

It is envisioned in the present invention that each culturing vessel may contain, localized differences in culture conditions. For example, the temperature of the culturing vessels may be independently controlled to optimize the growth conditions to the respective cell type cultured therein. Another example is that the culture medium may be altered locally to include additives to optimize growth conditions or for selected expression. In this example, it is envisioned that the additive can be added directly to the culturing vessel or can be added to the fluid feed line prior to entry into the culturing vessel.

Figure 3:
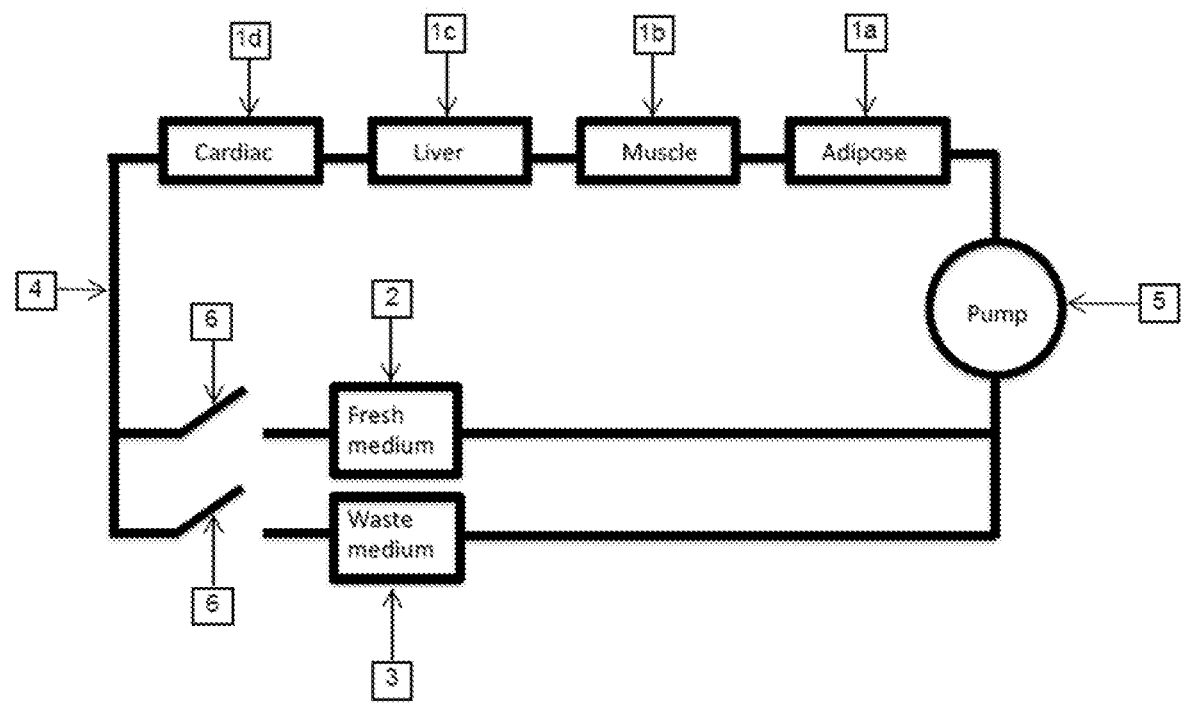
FIG. 3 shows an example of a large-scale combination cell culture system according to the present invention, wherein different cell types are cultured in separate culturing vessels and the culturing vessels are connected in series.

As used herein, "vessels connected in series" means two or more vessels are fed in series from a pump, in other words, a fluid flows from a pump through a first culturing vessel, then into a second culturing vessel, etc. and ultimately is looped back to the pump. As was the case with parallel culturing vessels, each culturing vessel may contain localized differences in culture conditions as described above. As shown in FIG. 3, culturing vessel 1a contains adipose cells, vessel, 1b contains muscle cells, vessel 1c contains liver cells and vessel 1d contains cardiac cells. The culturing vessels are connected to fresh medium vessel 2 and waste vessel 3 by line 4. Medium is pumped through the lines into the vessels with pump 5. The medium flows sequentially from vessel 1a to 1b to 1c to 1d. Valves 6 control the now to the vessels, when the valve to the fresh medium vessel is open, the valve to the waste vessel is closed and visa versa.

Figure 4:
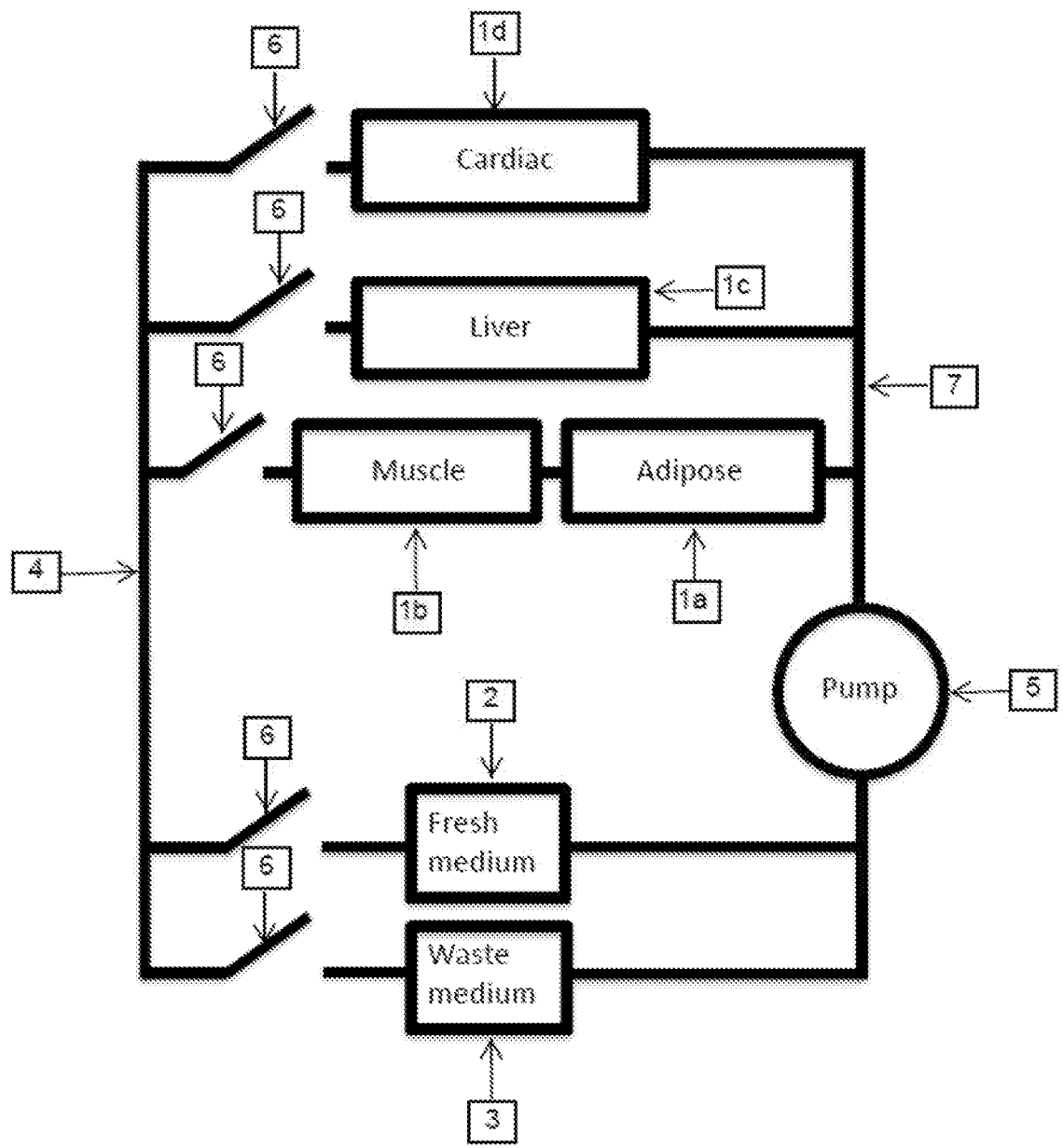
FIG. 4 shows an example of a large-scale cell culture system according to the present invention, wherein different cell types are cultured in separate culturing vessels where some are connected in series (e.g., muscle cells and adipose cells) and others are connected in parallel (e.g., liver cells and cardiac cells) within the same system.

Within the parallel method, the in series method, or the mixed method, it is envisioned that a conditioned medium or a medium containing cultured cell mass may be obtained from each of the respective culturing vessels or even just from the final culturing vessel. It is also envisioned that the conditioned medium may be recovered from the fresh medium vessel or from a recovery outlet or outlet port installed within the circuit. Shown in FIG. 4 is a combination of a parallel and an in series system, culturing vessel 1a contains adipose cells, vessel 1b contains muscle cells, vessel 1c contains liver cells and vessel 1d contains cardiac cells. The culturing vessels are connected to fresh medium vessel 2 and waste vessel 3 by line 4. Medium is pumped through the lines 4 into the vessels with pump 5. The medium flows from the pump to the manifold through line 4, then in parallel through vessel 1a, 1c and 1d. Then the medium flows sequentially from vessel 1a to 1b. Valves 6 control the flour to the vessels, when the valve to the fresh medium vessel is open, the valve to the waste vessel is closed and visa versa.

As used herein, conditioned medium is medium harvested from cultured cells. It contains metabolites, growth factors, extracellular matrix proteins, cytokines, etc. secreted into the medium by the cultured cells. This selective collection allows tuning of the properties of the conditioned medium. For example, it may be envisioned that the first culturing vessel is used to culture one cell type (e.g., muscle cells) and that the culture medium containing, for example cytokines and growth factors, from that culturing vessel can be fed into the subsequent culturing vessel for growth of a second cell type (e.g., adipose cells) or a mixture of a second cell type and the first cell type (e.g., adipose cells and muscle cells). This can be repeated in subsequent culturing vessels in series or in parallel. In each culturing, vessel it may be desired to supplement fresh basal or growth, medium from, a secondary feed line. Of course, other nutrients, salts, hormones, factors, etc. may also be fed individually or in combination independently into each culturing vessel in the network. In this embodiment it is envisioned that a membrane may be fitted between subsequent culturing vessels to ensure that no or very little cells pass between culturing vessels.

Regardless of whether using the parallel method, the in series method or the mixed method, conditioned medium can be obtained by having the circuit closed (i.e., medium is allowed to flow through) to the fresh medium vessel and open (i.e., medium is prevented from flowing through) to the waste medium vessel and allowing the culture to grow with constant circulation through the system for a time and under suitable conditions to reach the desired growth conditions (e.g. for meat applications a desired cell density of at least $1 \times 10^7$ cells/cc and for personal care products a certain composition related to metabolites, growth factors, and/or extracellular matrix proteins). In this method, the conditioned medium can be recovered from any location in the growth circuit. Preferably, the conditioned medium is recovered from the fresh medium vessel or from a recovery outlet or outlet port included in the circuit.

In a modification to the foregoing, it is envisioned that, at either predetermined time intervals or based on reached established medium benchmarks (e.g., cell density or composition of the conditioned medium), a percentage of the medium in the waste medium vessel is removed and replaced with fresh basal medium added to the fresh medium vessel and/or removed, purified, and returned to the fresh medium vessel. For example, the percentage of medium to be exchanged can be at least 2.5%, at least 5%, at least 7.5%, at least 10%, at least 12.5%, at least 15%, at least 17.5%, at least 20% to at most 25%, at most 22.5%, at most 20%, at most 17.5%, at most 15%, at most 12.5% and all points, ranges and sub-ranges defined by these lower and upper limits. In this variant of the method, when purifying or replacing part of the waste medium with fresh medium, the fresh medium vessel should be closed to media flow. This physically allows the addition of new medium into it, which is much more difficult if the liquid is flowing through it. Also, by closing the fresh medium vessel to liquid flow, all of the medium in the system flows through the waste collecting vessel which facilitates draining and replacement in a controlled manner (e.g. let 2.5% out and put that 2.5% back into the fresh medium vessel).

In another modification to either of the foregoing, it is envisioned that the waste medium vessel is connected to a dialyzer to filter out waste from the medium and the treated medium is then returned to the system.

The culturing vessels may, independently, range in size from about 0.5 liter to greater than 100,000 liters. In an embodiment of the present invention the culturing vessels independently range in size from 0.5 liters to 250,000 liters, from 1 liters to 100,000 liters, from 2 liters to 50,000 liters, from 5 liters to 25,000 liters, from 10 liters to 10,000 liters, from 25 liters to 5,000 liters, from 50 liters to 2,500 liters, from 100 liters to 1,000 liters; within this invention the ranges are listed as merely exemplary and the lower limits and upper limits may be selected to define alternative ranges.

Although not particularly limited, the number of culturing vessels may range from 1 to about 50. The range can have a lower limit of 2, 3, 4, 5, 6, 7, 8, 9, and 10 and an upper limit of 45, 40, 35, 30, 25, and 20, inclusive of all ranges and sub-ranges and particular values that may be defined by this particular values.

Suitable pumps are known in the art. Piping is used to connect the pump to the vessels and the vessels to each other. Suitable piping is known in the art and includes polyvinyl chloride (PVC), stainless steel, tubes, pipes, lines, hoes and the like. The piping may contain or be connected to heating units.

The vessels may be provided with means for heating the fluid or inline heating may be utilized. A separate vessel may be used for fresh medium; the fresh medium vessel may be connected to the system with a valve that is open to provide fresh medium to the system when desired. Another separate vessel may be used for waste collection; the waste vessel may be connected to the system with a valve that is open to remove waste from the system when desired.

In general, the method described herein may be used to culture cells, and particularly muscle (e.g., smooth muscle) and fat cells to form engineered meat. The method includes providing a culture system, transferring basal medium or basal medium supplemented with non-animal derived growth factors and other components as might be needed for the efficient growth of cells, into the culturing, vessels, adding cells and culturing the cells to produce a conditioned medium. The basal medium (e.g. Dulbecco's Modified Eagle Medium; DMEM) may include water, salts, vitamins, minerals, amino acids and a carbon source such as glucose. In an embodiment of the invention, the basal medium of the current invention does not include animal derived serum such as fetal bovine serum, calf serum or horse serum. As used herein, by "does not include animal serum" or "animal serum-free" is meant that the medium contains less than about 1% or less than about 0.5% or less than about 0.1% or less than about 0.01% or zero animal derived serum by total weight of the medium. It is envisioned within the invention that the serum-free medium may contain growth factors and other substances, but nothing derived from an animal.

At least one type of cell is added to each culturing vessel. Suitable types of cells include but are not limited to muscle, fat, cartilage, liver, heart, kidney, lung, endothelial and combinations thereof. Other types of mammalian cells may also be used within the present invention. Suitable cells may be obtained by biopsy from fish, pig, cows, chicken, turkey, sheep, goat and the like. The various cell types, or their combination, in the separate culturing vessels, connected through common circulation secrete cell and tissue specific growth factors and cytokines into the basal medium thus rendering it conditioned.

The various specialized primary animal cells, such as muscle or fat to be added and subsequently expanded in the culturing vessels may be obtained via biopsy from live animals. Alternatively, the starter cells may be stem cells of various origin, such as satellite cells or induced pluripotent stem cells (iPS cells) and culture conditions may be adjusted to develop these stem cells into the desired cell types. The starter cells in the individual culturing vessels may also be genetically modified cells such as immortalized cells allowing for unlimited number of cell divisions without any change in cell behavior.

The method of the present invention may include utilizing gases to optimize growth conditions independently in each culturing vessel or throughout the entirety of the system. Suitable gases include but are not limited to oxygen, carbon dioxide and the like.

In one embodiment, the culture system is used to culture muscle, fat and cartilage cells. Salts are used to optimize growth conditions for cells. Suitable salts include but are not limited to those of sodium, potassium, calcium and the like. The amount of salt used is consistent with ranges known in the art of tissue or cell culture. Cells need nutrients to grow; nutrients provide a source of carbon. Suitable carbon sources include but are not limited to glucose, glycerol, galactose, hexose, fructose, pyruvate, glutamine and the like. The amount of carbon source used is consistent with ranges known in the art of tissue or cell culture. The basal medium may also include buffer such as phosphate-buffered saline (PBS), tris(hydroxymethyl)aminomethane (TRIS), phosphate-citrate buffer, sorensen's phosphate buffer, sodium citrate buffer, 4-(2-hydroxyethyl)-1-piperazineethanesulfonic acid (HEPES) and the like. Alternatively, carbon dioxide can be fed into the medium to control the pH. The pH is maintained at about 5.5 to about 7.5. Vitamins are used to optimize growth conditions for cells. Suitable vitamins include but are not limited to folic acid, nicotinamide, riboflavin, $B_{12}$ and the like. The amount of vitamins used is consistent with ranges known in the art of tissue or cell culture. Therefore, as stated above, the localized culture conditions can be independently controlled to optimize the growth of the cells within the respective culturing vessels.

Culture conditions can be further controlled by temperature. Even though mammalian cells are typically cultured at body temperature, that is at 37° C., sometimes deviation from this temperature might be desirable, depending on cell type. Thus the culturing vessels may be individually temperature controlled in the range of 20-38° C. (from room temperature to near body temperature). However, exemplary conditions may include incubating the culturing vessels to a temperature ranging from 20° C. to 45° C., 32° C. to 42° C. from 35° C. to 40° C., from 36° C. to 38° C., from 36.5° C. to 37.5° C., or 37° C., inclusive of all points, ranges and sub-ranges bound by the identified lower and upper limits. Further control and optimization of culturing can be achieved by the adjustment of the perfusion, its speed, pressure and, in case of pulsatile flow, its pulse frequency and strength.

In another embodiment, the basal medium contains water, sodium chloride, HEPES buffer and cells. The cells are muscle, fat and cartilage cells isolated from a biopsied tissue from livestock or poultry or stem cells (such as induced pluripotent stem cells, iPS cells or others). The biopsied tissue is digested to separate the individual cells. The cells are then loaded into the culturing vessels of the above-described culture system and cultured in the circulating basal medium or, if needed, initially, basal medium supplemented with plant based growth factors. The cells are then cultured (e.g., incubated at 37° C. or a temperature independently controlled for the localized optimization of growth in a culture and culture conditions preferred for the cell type).

As the cells are cultured they start producing cell and tissue specific growth factors and cytokines (as well as waste) and secrete them into the common circulation, with this rendering the medium conditioned. Conditioned medium is basal medium supplemented with growth factors, hormones and other biochemical molecules secreted by cultured cells. As used herein, basal medium is an unsupplemented growth medium used to culture microorganisms which do not need special nutrients. Basal medium typically includes water, salts, vitamins, minerals, amino acids and a carbon source such as glucose. Examples of growth factors include, but are not limited to fibroblast growth factors (FGF) and vascular endothelial growth factors (VEGF).

Consistent with the foregoing, the vessels in this system may be large capacity three dimensional bioreactors from about 0.5 liter to about 250,000 liters (or larger), the latter allowing to grow cell mass with trillions of cells with biomass in thousands of kg. The use of these bioreactors may enable the use of non adherent cells or adherent cells grown on floating microcarriers. An example of microcarriers that may be useful in the present invention is taught in U.S. Pat. No. 9,752,122, the disclosure of which is hereby incorporated by reference.

In another embodiment it maybe more advantageous to use multiple circuits with smaller bioreactors in each (for example 5 L), to mitigate the damage from possible contamination. This way possible contamination in one circuit does not lead to detrimental consequences.

In another embodiment the adherent cells are cultured in a stirred culturing vessel. Stirring makes the cells adhere to each other thus forming aggregates of increasing size. The substrate for the growth of the adherent cells thus is provided by the surface of the aggregates. With the increase of the size of the aggregate cells deep inside of the aggregates eventually become deprived of the culture medium: the aggregates develop a necrotic core. Since the biomass in the culturing vessels eventually is used for cultured meat products, necrotic cells are still useful. The above outlined approach allows the culturing of adherent cells in three dimensional bioreactors for the purposes of cultured meat without the need for specific microcarriers.

The method of the present invention utilizes several connected culturing vessels to simultaneously grow various types of cells, each releasing growth factors and nutrients. In an exemplary embodiment, when connected culturing vessels are utilized, the number of connected culturing vessels may range from about 2 to about 50. For example, the range can have a lower limit of 2, 3, 4, 5, 6, 7, 8, 9, and 10 and an upper limit of 45, 40, 35, 30, 25, and 20. For example, in one embodiment, three connected vessels are culturing vessels, connected to a fresh medium vessel, and a waste vessel and a pump in line to move medium between the culturing vessels. The culturing vessels may be perfused by basal medium. The vessels are maintained at a sufficient temperature to sustain growth and continuously agitated. For example, one of the culturing vessels may contain liver cells, another muscle cells and the third may contain adipose cells. In this exemplary embodiment of the present invention, the three culturing vessels may be arranged in parallel or in series relative to each other. It is also possible to establish a mixed parallel in series arrangement wherein, for example, the culturing vessel containing muscle cells and the culturing vessel containing adipose cells are arranged in series, while the culturing vessel containing liver cells is arranged in parallel with respect to the in series arrangement. A similar 4 culturing vessel example is exemplified in FIG. 3. It should be noted that the specific placement of the in series portion and the parallel portion is not limited. For example, the in series portion may be, relative to the pump, prior to all parallel circuits, between parallel circuits, or after the parallel circuits. It is also envisioned that each circuit may be simultaneously fed by the pump.

The pump may transfer basal medium from the fresh medium vessel and circulate the medium from one vessel to the next and so on. Suitable pumps include but are not limited to piston pumps and peristaltic pumps. Waste medium may be removed gradually from the system and replaced by fresh basal medium as needed. Fresh basal medium flows into the pump compartment and from there is circulated through the different culturing vessels. The cells are retained in their respective culturing vessels. To prevent cells from flowing to another culturing vessel, filters may be used in line. Suitable filters are known in the art. Waste may be eliminated from the system.

A percentage of the conditioned medium may be removed from the circuit into the waste vessel and fresh basal medium may be added. For example, 10-15% of the circulating medium maybe be replaced daily. As fresh medium fills the system, the valve to the fresh medium reservoir is open (the valve to the waste reservoir is closed). As medium is circulated through the system (mimicking blood flow), the cells in the various tissues grow in numbers. At the same time the various specialized cells (heart muscle, hepatocytes, adipocytes, myoblasts) secrete growth factors, nutrients and the like into the circulation.

Each cell type secretes cell/tissue specific molecules and conditions the medium. The method may hold as many different types of cells for simultaneous growth as there are culturing vessels. For example, if there are ten culturing vessels, it may be desirable to simultaneously grow from one to ten types of cells. This cell culturing system allows the simultaneous culturing and growth of several cell types. These cells secrete specialized chemicals (e.g. growth factors) that support the growth of all the cell types in the system (akin to how the circulatory system in the body maintains the proper functioning of all the organs, tissues and cells) in the body. In such a system only the basic "nutrients" (i.e. the basal medium) needs to be delivered from the outside. Such basal medium contains components, such as salts, minerals, glucose, etc. The expensive components are then produced by the cells in the system akin to what happens in the organism. Just as the circulatory system in the organism assures the maintenance and growth of a large number of cells (the adult human body contains about 37 trillion cells), the above described system allows, similarly, the culturing of a large number of cells in a semi-autonomous manner.

The control/optimization of the circulation/pumping of the cell culturing system may be controlled or automated via computers, pressure gauges, etc.

Following cell culturing the cells can be separated from the conditioned medium containing the secreted growth factors, etc. Separation may be achieved by many well-known techniques including, but not limited to, centrifugation and filtration.

The conditioned medium (filtrate) may be useful for personal care compositions and nutritional supplements. For personal care compositions, the conditioned medium may be applied to the skin. The conditioned medium may be made into a cream, a lotion, an ointment, a gel and the like. For the nutritional supplements, the conditioned medium may be purified and ingested. The conditioned medium may be made into a liquid, a tablet, a gel, a powder and the like.

The personal care compositions may provide formulations suitable for topical application to skin. The composition may further include a cosmetically-acceptable carrier. The cosmetically-acceptable carrier may comprise from about 50% to about 99%, by weight, of the composition (e.g., from about 80% to about 95%, by weight, of the composition). The compositions may be made into a wide variety of product types that include but are not limited to liquid compositions such as lotions, creams, gels, sticks, sprays, shaving creams, ointments, cleansing liquid washes and solid bars, pastes, powders, mousses, masks, peels, make-ups, and wipes. These product types may comprise several types of cosmetically acceptable carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in the present invention can be formulated as solutions. Solutions typically include an aqueous solvent (e.g., front about 50% to about 99% or from about 90% to about 95% of a cosmetically acceptable aqueous solvent). Topical compositions may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be useful in the personal care compositions. See International Cosmetic Ingredient Dictionary and Handbook, eds. Wenninger and McEwen, (The Cosmetic, Toiletry, and Fragrance Assoc., Washington, D.C., 7.sup.th Edition, 1997) (hereinafter "CTFA Handbook") which contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in the CTFA Handbook.

The personal care compositions may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, the CTFA Handbook.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% from 30% to about 70%) of water; and from about 1% to about 10% (e.g., from about 2% to about 5%) of an emulsifier(s).

Single emulsion skin care compositions, such as lotions and creams, of the oil-in-water type and water-in-oil type are well-known in the cosmetic art and are useful for the personal care compositions. Multiphase emulsion compositions, such as the water-in-oil-in-water type are also useful. In general, such single or multiphase emulsions contain water, emollients, and emulsifiers as essential ingredients.

The personal care compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ ethylene/styrene copolymer and hydrogenated ethylene/propylene/styrene copolymer. Such gels typically comprise between about 0.1% and 5%, by weight, of such gelling agents.

The personal care compositions useful in the subject invention may contain, its addition to the aforementioned components, a wide variety of additional oil-soluble materials and/or water-soluble materials conventionally used in compositions for use on the skin at their art-established levels.

The personal care compositions may be applied as needed and/or as part of a regular regimen ranging from application once a week up to one or more times a day (e.g., twice a day). The amount used will vary with the age and physical condition of the end user, the duration of the treatment, the specific compound, product, or composition employed, the particular cosmetically-acceptable carrier utilized, and like factors.

Alternatively, a new batch of cells may be introduced into the circuit, such as muscle, fat and cartilage cells. The cells are then incubated at a suitable temperature and conditions for as long as needed. (Primary mammalian cells can divide a large number of times, the number of divisions set by the Hayflick limit. Alternatively, primary cells may be immortalized that allows unlimited number of divisions.)

When the intent of the method is to produce a composition for use in being made into food products (e.g., a meat product) the cell growth density is monitored and the biomass is grown for a time and under conditions suitable to reach a cell density of at least $1\times10^7$ cells/cc, of at least $5\times10^7$ cells/cc, $1\times10^8$ cells/cc, of at least $5\times10^8$ cells/cc is reached. Exemplary conditions include incubating the culturing vessels to a temperature ranging from 20° C. to 45° C., 32° C. to 42° C., from 35° C. to 40° C., from 36° C. to 38° C. from 36.5° C. to 37.5° C., or 37° C., inclusive of all points, ranges and sub-ranges bound by the identified lower and upper limits. Exemplary incubation times are from 10 to 40 hours, from 16 to 36 hours, from 20 to 30 hours, from 22 to 28 hours, or from 24 to 26 hours inclusive of all points, ranges and sub-ranges bound by the identified lower and upper limits.

The biomass collected from the culture system may be made directly into food such as a pate, hot dog and the like. Alternatively, it may be mixed with plant based ingredients such as soy bean (in particular, sprouted soy), potato and the like to produce a mixed product and lowering production costs. The amount of biomass in the mixed product may range from about 50% to about 100% or from about 60% to about 90% or from about 70% to about 80%, etc. by weight, based on the total weight of the composition. More complex products, such as bacon, charcuterie, sausage, etc. may be engineered using methods of tissue engineering. Additional ingredients may be added to enhance texture, flavor and fragrance to the meat product. The biomass may be placed into a mold to produce a desired shape, such as meat loaf.

The collected cultured medium from the waste vessel can be purified, filtered and reused. Alternatively, it can be centrifuged and the concentrate may also be useful for personal care compositions and nutritional supplements. For personal care compositions, the concentrate may be applied to the skin. The concentrate may be made into a cream, a lotion, an ointment, a gel and the like. For the nutritional supplements, the concentrate, appropriately processed, may be ingested. The concentrate may be made into a liquid, a tablet, a gel, a powder and the like.

As a representation of the present invention is the following embodiments:

[1] A cell culture system comprising:
a pump; at least two culturing vessels; a fresh basal medium vessel; and a waste collecting vessel, wherein the culturing vessels, the fresh basal medium vessel and the waste collecting vessel are connected in parallel with means for enabling a serum-free medium to move between the vessels.

[2] The system of [1], wherein each culturing vessel contains a different type of cells selected from the group consisting of muscle, fat, cartilage, liver, heart, kidney, and lung and other mammalian cells.

[3] The system of [1], wherein a single culturing vessel contains multiple types of cells wherein the cells are selected from the group consisting of muscle, fat, cartilage, liver, heart, kidney, and lung, and other mammalian cells.

[4] A method for making conditioned medium comprising:
providing the system of [1] with a serum-free medium;
adding animal cells into the culturing vessels;
circulating the serum free medium between the vessels;
heating the system to a temperature suitable for culturing; and
agitating and incubating the cells in the vessels for a time sufficient to culture the cells to a desired cell density.

[5] The method of [4], wherein each culturing vessel contains a different type of cells selected from the group consisting of muscle, fat, cartilage, liver, heart, kidney, and lung, and other mammalian cells.

[6] The method of [4], wherein a single culturing vessel contains multiple types of cells wherein the cells are selected from the group consisting of muscle, fat, cartilage, liver, heart, kidney, and lung, and other mammalian cells.

[7] A method for making meat comprising:
providing the system of [1] with a serum-free medium;
adding animal cells into the culturing vessels;
circulating the serum-free medium between the vessels;
heating the system to a temperature suitable for culturing;
agitating and incubating the cells in the vessels for a time sufficient to culture the cells to a desired cell density;
separating the cells from the medium; and
forming the cells into meat.

[8] The method of [7], wherein each culturing vessel contains a different type of cells selected from the group consisting of muscle, fat, cartilage, liver, heart, kidney, and lung, and other mammalian cells.

[8] The method of [7], wherein a single culturing vessel contains multiple types of cells wherein the cells are selected from the group consisting of muscle, fat, cartilage, liver, heart, kidney, and lung, and other mammalian cells.

[10] A cell culture system comprising:
a sub-system comprising a pump, a fresh basal medium vessel, and a waste collecting vessel,
wherein the fresh basal medium vessel and the waste collecting vessel are connected in parallel with respect to each other; and
at least three culturing vessels
wherein at least two of the at least three culturing vessels are arranged in series relative to each other and at least one of the at least three culturing vessels are arranged in parallel relative to the culturing vessels arranged in series.

[11] A method for making meat comprising:
providing a cell culture system comprising a pump; at least one culturing vessel; a fresh basal medium vessel; and a waste collecting vessel, wherein the pump, the culturing vessels, the fresh basal medium vessel and the waste collecting vessel are connected with means for enabling a serum-free medium to move between the vessels;
adding animal cells into the culturing vessel;
circulating the serum-free medium between the vessels;
heating the system to a temperature suitable for culturing;
agitating and incubating the cells in the vessel for a time sufficient to culture the cells to a desired cell density;
separating the cells from the medium; and
forming the cells into meat.

[12] The method of [11], wherein the cells are selected from the group consisting of muscle, fat, cartilage, liver, heart, kidney, lung, and other mammalian cells and combinations thereof.

[13] The method of [11], wherein the culturing vessels are connected in series.

[14] The method of [11], wherein the culturing vessels are connected in parallel.

[15] The method of [11], wherein the cell culture system comprises a sub-system and at least three culturing vessels, wherein the cell culture system is arranged such that the sub-system comprises a pump, a fresh basal medium vessel, and a waste collecting vessel,
  wherein the fresh basal medium vessel and the waste collecting vessel which are connected in parallel with respect to each other; and
  with respect to the at least three culturing vessels at least two of the at least three culturing vessels are arranged in series relative to each other and at least one of the at least three culturing vessels is arranged in parallel relative to the culturing vessels arranged in series.

In the context of the present description, all publications, patent applications, patents and other references mentioned herein, if not otherwise indicated, are explicitly incorporated by reference herein in their entirety for all purposes as if fully set forth, and shall be considered part of the present disclosure in their entirety.

Unless otherwise defined, all technical and scientific terms used herein have the same meaning as commonly understood by one of ordinary skill in the art to which this disclosure belongs. In case of conflict, the present specification, including definitions, will control.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present, disclosure be limited to the specific values recited when defining a range.

Further, unless otherwise explicitly stated to the contrary, when one or multiple ranges or lists of items are provided, this is to be understood as explicitly disclosing any single stated, value or item in such range or list, and any combination thereof with any other individual value or item in the same or any other list.

When the term "about" is used, it is used to mean a certain effect or result can be obtained within a certain tolerance, and the skilled person knows how to obtain the tolerance. When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus.

Further, unless expressly stated to the contrary, "or" and "and/or" refers to an inclusive and not to an exclusive. For example, a condition A or B, or A and/or B, is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the disclosure. This description should be read to include one or at least one and the singular also includes the plural unless it is obvious that it is meant otherwise.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skilled in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of, values), +/−10% of the stated value (or range of values), etc. Any numerical range recited herein is intended to include all sub-ranges subsumed therein.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Method of Making Conditioned Medium

In a culturing vessel, DMEM and cells obtained by needle biopsy of a pig, cow, etc. are mixed to create a suspension. Carbon dioxide and oxygen are fed into the culturing vessel. The solution is heated up to 37° C. and agitated continuously for from 10 to 40 hours. Optical density measurements are made to determine when the conditioned medium is ready for use. Alternatively, the analytes in the medium may be measured using chromatography.

Example 2

Method of Making a Concentrate and a Filtrate

The solution from the Example 1 is separated into a fraction containing the cells and a fraction containing growth factors and nutrients. Fractionation is accomplished by filtering the solution into a concentrate containing the cells while the filtrate will contain the growth factors and nutrients.

Example 3

The filtrate from Example 2 containing growth factors and nutrients is useful for personal care applications such as anti-wrinkle serums, skin pigmentation serums, hydrating serums, and the like. Alternatively, the concentrate may also be used in personal care applications.

Example 4

Method of Making Meat Product

The concentrate from the Example 2 is useful for food applications such as pate, soups and the like. The concentrate can be dried further in molds to make steaks, bacon, meatballs and the like. Suitable drying methods may include but are not limited to baking, pulling vacuum, air drying, air frying, and the like. Additional ingredients may be added to enhance texture, flavor and fragrance to the food.

In this example, the biomass that is needed for the meat products comes from centrifuging the content of the culturing vessels. For example, the contents of one culturing vessel containing muscle, fat and chondrocyte cells, may be centrifuged to provide a biomass with the three different cell types.

Example 5

Method of Making Nutritional Supplements

The concentrate from Example 2 is freeze dried and pulverized into a powder and filled into a pill capsule. The powder may also be mixed with water, milk and/or fruits to make a beverage.

Numerous modifications and variations on the present invention are possible in light of the above teachings. It is, therefore, to be understood that within the scope of the accompanying claims, the invention may be practiced otherwise than as specifically described herein.

We claim:

1. A method for making meat comprising: providing a cell culture system comprising a pump; at least one culturing vessel; a fresh basal medium vessel; and a waste collecting vessel, wherein the pump, the culturing vessels, the fresh basal medium vessel and the waste collecting vessel are connected with means for enabling a serum-free medium to move between the vessels; adding adherent animal cells into the culturing vessel, wherein the adherent animal cells are selected from the group consisting of: muscle cells, fat cells, cartilage cells, liver cells, heart cells, kidney cells, endothelial cells, and lung cells; circulating the serum-free medium between the vessels; heating the system to a temperature suitable for culturing; agitating and incubating the cells in the vessel, without a microcarrier, for a time sufficient for the cells to adhere to each other to form cellular aggregates of a desired cell density; separating the cells from the medium; and forming the cells into meat.

2. The system of claim 1, wherein the at least one culturing vessel contains multiple types of cells, wherein the multiple types of cells are selected from the group consisting of: muscle cells, fat cells, cartilage cells, liver cells, heart cells, kidney cells, endothelial cells, lung cells.

3. The method of claim 1, comprising at least two culturing vessels, wherein the at least two culturing vessels are connected in series.

4. The method of claim 3, wherein each culturing vessels independently contains a type of cell selected from the group consisting of: muscle cells, fat cells, cartilage cells, liver cells, heart cells, kidney cells, endothelial cells, and lung cells, and wherein the type of cell in each culturing vessel is different.

5. The method of claim 1, comprising at least two culturing vessels, wherein the at least two culturing vessels are connected in parallel.

6. The method of claim 1, wherein the cell culture system comprises a sub-system and at least three culturing vessels, wherein the cell culture system is arranged such that the sub-system comprises a pump, a fresh basal medium vessel, and a waste collecting vessel, wherein the fresh basal medium vessel and the waste collecting vessel which are connected in parallel with respect to each other; and with respect to the at least three culturing vessels at least two of the at least three culturing vessels are arranged in series relative to each other and at least one of the at least three culturing vessels is arranged in parallel relative to the culturing vessels arranged in series.

7. The method of claim 1, comprising circulating the serum-free medium between the vessels, wherein the circulation is for perfusion of the medium.

8. The method of claim 1, wherein the desired cell density is at least $1 \times 10^7$ cells/cc (cubic cm) of the medium.

9. The method of claim 1, wherein the volume of the at least one culturing vessel is at least 0.5 liter.

10. A method for making meat comprising: providing a cell culture system comprising a pump; at least one culturing vessel; a fresh basal medium vessel; and a waste collecting vessel, wherein the pump, the culturing vessel, the fresh basal medium vessel and the waste collecting vessel are connected with means for enabling a culture medium to move between the vessels; adding adherent animal cells into the culturing vessel, wherein the adherent animal cells are selected from the group consisting of: muscle cells, fat cells, cartilage cells, liver cells, heart cells, kidney cells, endothelial cells, and lung cells; circulating the culture medium between the vessels; heating the system to a temperature suitable for culturing; agitating and incubating the cells in the vessel, without a microcarrier, for a time sufficient for the cells to adhere to each other to form cellular aggregates of a desired cell density; separating the cells from the medium; and forming the cells into meat.

* * * * *